(12) United States Patent
Ding (10) Patent No.: US 9,345,814 B2
(45) Date of Patent: *May 24, 2016

(54) METHACRYLATE COPOLYMERS FOR MEDICAL DEVICES

(71) Applicant: Abbott Cardiovascular Systems Inc., Santa Clara, CA (US)

(72) Inventor: Ni Ding, San Jose, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/678,867

(22) Filed: Apr. 3, 2015

(65) Prior Publication Data

US 2015/0209486 A1    Jul. 30, 2015

Related U.S. Application Data

(63) Continuation of application No. 10/957,265, filed on Sep. 30, 2004, now Pat. No. 9,011,831.

(51) Int. Cl.
*A61L 31/10* (2006.01)
*A61L 31/16* (2006.01)

(52) U.S. Cl.
CPC .............. *A61L 31/10* (2013.01); *A61L 31/16* (2013.01); *A61L 2300/114* (2013.01); *A61L 2300/222* (2013.01); *A61L 2300/254* (2013.01); *A61L 2300/416* (2013.01); *A61L 2300/426* (2013.01); *A61L 2300/606* (2013.01); *A61L 2420/06* (2013.01)

(58) Field of Classification Search
CPC ... A61L 31/10; A61L 31/16; A61L 2300/114; A61L 2300/222; A61L 2300/254; A61L 2300/416; A61L 2300/606; A61L 2300/426; A61L 2420/06; C08L 33/12
See application file for complete search history.

(56) References Cited

U.S. PATENT DOCUMENTS

| 3,886,125 A | 5/1975 | Chromecek |
| 4,375,810 A | 3/1983 | Belykh et al. |

(Continued)

FOREIGN PATENT DOCUMENTS

| DE | 2947985 | 9/1981 |
| EP | 2316500 | 5/2011 |

(Continued)

OTHER PUBLICATIONS

U.S. Appl. No. 10/376,348, filed Feb. 26, 2003, Ding et al.

(Continued)

*Primary Examiner* — Blessing M Fubara
(74) *Attorney, Agent, or Firm* — Squire Patton Boggs (US) LLP (57) ABSTRACT

A polymer of hydrophobic monomers and hydrophilic monomers is provided. It is also provided a polymer blend that contains the polymer and another biocompatible polymer. The polymer or polymer blend and optionally a biobeneficial material and/or a bioactive agent can form a coating on an implantable device such as a drug delivery stent. The implantable device can be used for treating or preventing a disorder such as atherosclerosis, thrombosis, restenosis, hemorrhage, vascular dissection or perforation, vascular aneurysm, vulnerable plaque, chronic total occlusion, patent foramen ovale, claudication, anastomotic proliferation for vein and artificial grafts, bile duct obstruction, ureter obstruction, tumor obstruction, or combinations thereof.

35 Claims, 1 Drawing Sheet

(56) References Cited

U.S. PATENT DOCUMENTS

| | | |
|---|---|---|
| 4,931,287 A | 6/1990 | Bae et al. |
| 5,019,096 A | 5/1991 | Fox, Jr. et al. |
| 5,053,469 A | 10/1991 | Tatemoto et al. |
| 5,071,725 A | 12/1991 | Kubo et al. |
| 5,159,051 A | 10/1992 | Onwumere et al. |
| 5,163,952 A | 11/1992 | Froix |
| 5,219,945 A | 6/1993 | Dicker et al. |
| 5,258,020 A | 11/1993 | Froix |
| 5,464,650 A | 11/1995 | Berg et al. |
| 5,607,467 A | 3/1997 | Froix |
| 5,616,338 A | 4/1997 | Fox, Jr. et al. |
| 5,624,411 A | 4/1997 | Tuch |
| 5,650,170 A | 7/1997 | Wright et al. |
| 5,674,242 A | 10/1997 | Phan et al. |
| 5,723,219 A | 3/1998 | Kolluri et al. |
| 5,759,205 A | 6/1998 | Valentini |
| 5,821,343 A | 10/1998 | Keogh |
| 5,824,049 A | 10/1998 | Ragheb et al. |
| 5,843,156 A | 12/1998 | Slepian et al. |
| 5,869,127 A | 2/1999 | Zhong |
| 5,873,904 A | 2/1999 | Ragheb et al. |
| 5,879,713 A | 3/1999 | Roth et al. |
| 5,932,299 A | 8/1999 | Katoot |
| 5,962,138 A | 10/1999 | Kolluri et al. |
| 5,993,972 A | 11/1999 | Reich et al. |
| 5,997,517 A | 12/1999 | Whitbourne |
| 6,096,070 A | 8/2000 | Ragheb et al. |
| 6,099,563 A | 8/2000 | Zhong |
| 6,110,483 A | 8/2000 | Whitbourne et al. |
| 6,143,354 A | 11/2000 | Koulik et al. |
| 6,153,252 A | 11/2000 | Hossainy et al. |
| 6,159,978 A | 12/2000 | Myers et al. |
| 6,179,817 B1 | 1/2001 | Zhong |
| 6,180,632 B1 | 1/2001 | Myers et al. |
| 6,197,051 B1 | 3/2001 | Zhong |
| 6,214,901 B1 | 4/2001 | Chudzik et al. |
| 6,231,590 B1 | 5/2001 | Slaikeu et al. |
| 6,245,760 B1 | 6/2001 | He et al. |
| 6,248,129 B1 | 6/2001 | Froix |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,277,449 B1 | 8/2001 | Kolluri et al. |
| 6,299,604 B1 | 10/2001 | Ragheb et al. |
| 6,306,166 B1 | 10/2001 | Barry et al. |
| 6,306,176 B1 | 10/2001 | Whitbourne |
| 6,335,029 B1 | 1/2002 | Kamath et al. |
| 6,344,035 B1 | 2/2002 | Chudzik et al. |
| 6,383,500 B1 | 5/2002 | Wooley et al. |
| 6,387,379 B1 | 5/2002 | Goldberg et al. |
| 6,437,040 B2 | 8/2002 | Anthony et al. |
| 6,482,834 B2 | 11/2002 | Spada et al. |
| 6,503,494 B1 | 1/2003 | Cauwet-Martin et al. |
| 6,506,837 B2 | 1/2003 | Destarac et al. |
| 6,524,347 B1 | 2/2003 | Myers et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,579,947 B2 | 6/2003 | Heitz et al. |
| 6,696,089 B2 | 2/2004 | Kabanov et al. |
| 6,723,815 B2 | 4/2004 | Callaghan et al. |
| 6,753,083 B2 | 6/2004 | Mistry et al. |
| 6,884,547 B2 | 4/2005 | Mori et al. |
| 6,926,919 B1 | 8/2005 | Hossainy et al. |
| 7,005,137 B1 | 2/2006 | Hossainy et al. |
| 7,008,979 B2 | 3/2006 | Schottman et al. |
| 7,094,256 B1 | 8/2006 | Shah et al. |
| 7,217,426 B1 | 5/2007 | Hossainy et al. |
| 7,226,612 B2 | 6/2007 | Sohier et al. |
| 7,244,443 B2 * | 7/2007 | Pacetti ........................... 424/423 |
| 7,247,313 B2 | 7/2007 | Roorda et al. |
| 7,357,793 B2 | 4/2008 | Pacetti |
| 7,396,539 B1 | 7/2008 | Hossainy et al. |
| 7,498,044 B2 | 3/2009 | Petereit et al. |
| 7,563,454 B1 | 7/2009 | Pacetti et al. |
| 7,766,884 B2 * | 8/2010 | Pacetti ........................... 604/265 |
| 7,833,544 B2 | 11/2010 | Lewis et al. |
| 8,309,112 B2 * | 11/2012 | Glauser et al. ................. 424/422 |
| 8,658,194 B2 | 2/2014 | Glauser et al. |
| 9,011,831 B2 * | 4/2015 | Ding ........................... 424/78.27 |
| 2001/0007083 A1 | 7/2001 | Roorda |
| 2001/0009688 A1 | 7/2001 | Dinh et al. |
| 2001/0014717 A1 | 8/2001 | Hossainy et al. |
| 2001/0020011 A1 | 9/2001 | Mathiowitz et al. |
| 2001/0029351 A1 | 10/2001 | Falotico et al. |
| 2001/0051608 A1 | 12/2001 | Mathiowitz et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0013437 A1 | 1/2002 | McKee et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0041899 A1 | 4/2002 | Chudzik et al. |
| 2002/0051730 A1 | 5/2002 | Bodnar et al. |
| 2002/0082679 A1 | 6/2002 | Sirhan et al. |
| 2002/0111590 A1 | 8/2002 | Davila et al. |
| 2002/0123801 A1 | 9/2002 | Pacetti et al. |
| 2002/0165608 A1 | 11/2002 | Llanos et al. |
| 2002/0176849 A1 | 11/2002 | Slepian |
| 2002/0188037 A1 | 12/2002 | Chudzik et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0036794 A1 | 2/2003 | Ragheb et al. |
| 2003/0039689 A1 | 2/2003 | Chen et al. |
| 2003/0040790 A1 | 2/2003 | Furst |
| 2003/0060877 A1 | 3/2003 | Falotico et al. |
| 2003/0065377 A1 | 4/2003 | Davila et al. |
| 2003/0083646 A1 | 5/2003 | Sirhan et al. |
| 2003/0083739 A1 | 5/2003 | Cafferata |
| 2003/0208013 A1 | 11/2003 | Callaghan et al. |
| 2004/0063805 A1 | 4/2004 | Pacetti et al. |
| 2004/0117007 A1 | 6/2004 | Whitbourne et al. |
| 2004/0144655 A1 | 7/2004 | Bertrand et al. |
| 2004/0167597 A1 | 8/2004 | Costantino et al. |
| 2005/0208093 A1 | 9/2005 | Glauser et al. |
| 2006/0078493 A1 | 4/2006 | von Oepen |

FOREIGN PATENT DOCUMENTS

| | | |
|---|---|---|
| EP | 1802359 | 1/2012 |
| JP | Shouwa 61 (1986)161207 | 7/1986 |
| JP | Heisei 04 (1992)325160 | 11/1992 |
| JP | 2006-504498 | 2/2006 |
| JP | 2007-534652 | 11/2007 |
| WO | WO 89/06957 | 8/1989 |
| WO | WO 98/04605 | 2/1998 |
| WO | WO 03/092732 | 11/2003 |
| WO | WO 03/106518 | 12/2003 |
| WO | WO 04/000383 | 12/2003 |
| WO | WO 2004/009145 | 1/2004 |
| WO | WO 2004/026359 | 4/2004 |
| WO | WO 2004/043320 | 5/2004 |
| WO | WO 2004/096185 | 11/2004 |
| WO | WO 2005/063710 | 7/2005 |
| WO | WO 2006/039152 | 4/2006 |

OTHER PUBLICATIONS

International Search Report and Written Opinion for application PCT/US2005/033660, mailed Jan. 27, 2006, 13 pgs.
Translation of the Notification of Refusal from JPO for appl. No. JP2007-534652, mailed Aug. 7, 2012, 2 pgs.

* cited by examiner

METHACRYLATE COPOLYMERS FOR MEDICAL DEVICES

CROSS-REFERENCE TO RELATED APPLICATIONS

This application is a continuation of U.S. patent application Ser. No. 10/957,265, filed on Sep. 30, 2004, published as U.S. Patent Application Publication No. US 2006-0067908 A1 on Mar. 30, 2006, and issuing as U.S. Pat. No. 9,011,831 B2 on Apr. 21, 2015, which is hereby incorporated by reference in its entirety, expressly including any drawings, and is incorporated by reference for all purposes.

BACKGROUND OF THE INVENTION

1. Field of the Invention

This invention generally relates to a polymeric material useful for an implantable device, such as a stent.

2. Description of the Background

Although stents work well mechanically, the chronic issues of restenosis and, to a lesser extent, stent thrombosis remain. Pharmacological therapy in the form of a drug delivery stent appears to be a feasible means to tackle these issues. Polymeric coatings placed onto the stent serve to act both as the drug reservoir and to control the release of the drug. One of the commercially available polymer coated products is stents manufactured by Boston Scientific. For example, U.S. Pat. Nos. 5,869,127; 6,099,563; 6,179,817; and 6,197,051, assigned to Boston Scientific Corporation, describe various compositions for coating medical devices. These compositions provide to stents described therein an enhanced biocompatibility and may optionally include a bioactive agent. U.S. Pat. No. 6,231,590 to Scimed Life Systems, Inc., describes a coating composition, which includes a bioactive agent, a collagenous material, or a collagenous coating optionally containing or coated with other bioactive agents.

The nature of the coating polymers plays an important role in defining the surface properties of a coating. For example, a very low $T_g$, amorphous coating material can have unacceptable rheological behavior upon mechanical perturbation such as crimping, balloon expansion, etc. On the other hand, a high $T_g$ or highly crystalline coating material introduces brittle fractures in the high strain areas of the stent pattern. For example, methacrylate or methacrylate polymers have been used as coating materials partially because that they have an alternate tertiary backbone structure which imparts stability to the polymer as a result of the stability of the C—C bond. This stability renders the polymer relatively impervious to attack by free radicals. However, poly(methyl methacrylate) (PMMA), a commonly used methacrylate polymer, is a hard material ($T_g$=85° C. to 105° C.) with low elongation (about 4%). Another common methacrylate polymer, poly(butyl methacrylate) (PBMA), is relatively soft ($T_g$=25–35° C.), but also has low elongation. A coating formed of a PMMA/PBMA blend, or block or random copolymer thereof, would be softer than a coating formed of a pure PMMA, but would have better elongation than PMMA. In addition, both PMMA and PBMA are hydrophobic polymers. A coating formed of either polymer or a blend of the two polymers would have relatively low water uptake (about 0.4%) and would be relatively impermeable to certain drugs. A membrane formed by said polymer or polymer blend would be quite impermeable to poorly water soluble drugs such as paclitaxel, sirolimus and everolimus, etc. Such a coating would have limited application.

The present invention addresses such problems by providing a polymeric material for coating implantable devices. By balancing hydrophilic and hydrophobic components, a variety of drugs can be delivered in a controllable manner.

SUMMARY OF THE INVENTION

Provided herein is a polymer formed of hydrophobic monomers and hydrophilic monomers. The polymer contains tertiary carbon groupings in its backbone, for example, having an alternate tertiary carbon backbone structure. The hydrophilic monomers impart drug permeability to the polymer, and can provide additional biobeneficial properties. The properties of the polymer can thus be tuned by varying the ratio of hydrophobic and hydrophilic monomers.

The polymer can form a coating on an implantable device. Alternatively, the polymer can be blended with one or more other biocompatible polymers such as another methacrylate polymer to form the coating. In some embodiments, the polymer or polymer blend can be used to form an implantable device itself. The coating and/or the implantable device can optionally include a biobeneficial material and/or a bioactive agent.

The implantable device or coating can optionally include a bioactive agent. Some exemplary bioactive agents are paclitaxel, docetaxel, estradiol, nitric oxide donors, super oxide dismutases, super oxide dismutases mimics, 4-amino-2,2,6, 6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy] ethyl-rapamycin, and 40-O-tetrazole-rapamycin, ABT-578, clobetasol, prodrugs thereof, co-drugs thereof, and combinations thereof. The implantable device can be implanted in a patient to treat or prevent a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

DETAILED DESCRIPTION

Provided herein is a polymer formed of hydrophobic monomers and hydrophilic monomers. The polymer contains tertiary carbon groupings in its backbone, for example, having an alternate tertiary carbon backbone structure. The hydrophilic monomers impart drug permeability to the polymer, and can provide additional biobeneficial properties. The properties of the polymer can thus be tuned by varying the ratio of hydrophobic and hydrophilic monomers.

As used herein, the term "tertiary carbon grouping" means a carbon grouping having three carbo substituents attached to a carbon atom, and the remaining valency of the carbon atom is used by the carbon atom to attach to another chemical grouping or moiety.

The polymer can form a coating on an implantable device. Alternatively, the polymer can be blended with one or more other biocompatible polymers such as another methacrylate polymer to form the coating. In some embodiments, the polymer or polymer blend can be used to form an implantable device itself. The coating and/or the implantable device itself can optionally include a biobeneficial material and/or a bioactive agent.

The implantable device or coating can optionally include a bioactive agent. Some exemplary bioactive agents are paclitaxel, docetaxel, estradiol, nitric oxide donors, super oxide dismutases, super oxide dismutases mimics, 4-amino-2,2,6, 6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy] ethyl-rapamycin, and 40-O-tetrazole-rapamycin, ABT-578, clobetasol, prodrugs thereof, co-drugs thereof, and combinations thereof. The implantable device can be implanted in a patient to treat or prevent a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

Polymers of Hydrophobic Monomers and Hydrophilic Monomers

In one embodiment, the hydrophobic monomers and hydrophilic monomers are capable of forming homopolymers having different Tgs. For example, the hydrophobic monomer is capable of forming a homopolymer with a $T_g$ above the room temperature, and the hydrophilic monomer is capable of forming a homopolymer having a $T_g$ below the room temperature. By varying the ratio of these two monomers, one can form a copolymer containing these two monomers with a $T_g$ at, for example, 37° C.

When the properties of hydrophobic monomer and hydrophilic monomer are drastically different, randomness of the copolymer would decrease during free-radical polymerization and may lead to two glass transition temperatures for the copolymer. In one embodiment, one glass transition temperature can be below, for example, about 37° C., and the other can be above, for example, about 37° C.

The hydrophobic monomer can be in the range of, e.g., from above 0 mole % to below 100 mole %, and the hydrophilic monomer can be in the range from below 100 mole % to above 0 mole %. More specifically, the hydrophobic monomer can be in the range of, e.g., from about 10 mole % to about 90 mole % or from about 20 mole % to about 80 mole %, and the hydrophilic monomer can be in the range from about 90 mole % to about 10 mole % or from about 80 mole % to about 20 mole %.

The hydrophobic monomers useful for forming the polymer are for example, a vinyl monomer having a tertiary carbon having a general formula of $(R_1)(R_2)C=CH_2$ where $R_1$ and $R_2$ are non-hydrogen groups. In one embodiment, the hydrophobic monomer can be any methacrylate, or fluorinated methacrylate monomers. Alternatively, the hydrophobic monomers can be acrylate, or fluorinated acrylate monomers. As another alternative, the hydrophobic monomers can be 2-phenylacrylate or 2-phenylacrylamide. The ester group in these hydrophobic monomers can have a short chain alkyl group ranging from C1 to C6. Examples of fluorinated methacrylate monomer are 1H,1H,2H,2H-heptadecafluorodecyl methacrylate, 1H,1H,3H-hexafluorobutyl methacrylate.

The hydrophilic monomers can be any vinyl monomer having one or more hydrophilic groups, methacrylamide or acrylamide. Some examples of the hydrophilic groups are pyrrolidone group(s), carboxylic acid group(s), sulfone group(s), sulfonic acid group(s), amino group(s), alkoxy group(s), amide group(s), ester group(s), acetate group(s), poly(ethylene glycol) group(s), poly(propylene glycol) group(s), poly(tetramethylene glycol) group(s), poly(alkylene oxide) group(s), hydroxyl group(s), or a substituent that bears a charge and/or any of pyrrolidone group(s), carboxylic acid group(s), sulfone group(s), sulfonic acid group(s), amino group(s), alkoxy group(s), amide group(s), ester group(s), acetate group(s), poly(ethylene glycol) group(s), poly(propylene glycol) group(s), poly(tetramethylene glycol) group(s), poly(alkylene oxide) group(s), and hydroxyl group(s). Some exemplary hydrophilic monomers are vinyl pyrrolidone, hydroxyethyl methacrylate, hydroxypropyl methacrylate, methyl vinyl ether, alkyl vinyl ether, vinyl alcohol, methacrylic acid, acrylic acid, acrylamide, N-alkyl acrylamide, hydroxypropylmethacrylamide, vinyl acetate, 2-sulfoethyl methacrylate, 3-sulfopropyl acrylate, 3-sulfopropyl methacrylate, and PEG-methacrylate. Some exemplary substituents bearing a charge can be, for example, choline, phosphoryl choline, 2-aminoethyl methacrylate hydrochloride, N-(3-aminopropyl)methacrylamide hydrochloride, 2-N-morpholinoethyl methacrylate, vinylbenzoic acid, vinyl sulfonic acid, and styrene sulfonates.

In one embodiment, the polymer has a general formula as shown below (Formula I):

where m and n can be positive integers ranging from, e.g., 1 to 100,000, the hydrophobic monomer can be a methacrylate or fluorinated methacrylate, and the hydrophilic monomer can be any monomer having a hydrophilic group. The polymer has an alternate tertiary carbon backbone structure and can be a random or block polymer.

In another embodiment, the polymer has a general formula as shown below (Formula II):

where m, n, p can be positive integers ranging from, e.g., 1 to 100,000, the hydrophobic monomer can be a methacrylate or fluorinated methacrylate, and the hydrophilic monomer can be any monomer having a hydrophilic group. The polymer has an alternate tertiary carbon backbone structure and can be a random or block polymer.

In another embodiment, the polymer has a general formula as shown below (Formula III):

where m, n, p can be positive integers ranging from, e.g., 1 to 100,000, the hydrophobic monomer can be a methacrylate or fluorinated methacrylate, and the hydrophilic monomer can be any monomer having a hydrophilic group. The polymer has an alternate tertiary carbon backbone structure and can be a random or block polymer.

Any hydrophobic methacrylate monomer can be used to form the polymer of Formula I. In one embodiment, the hydrophobic methacrylate monomer has a short alkyl group from e.g., C1-C6 and can be, for example, methyl methacrylate, ethyl methacrylate, propyl methacrylate, iso-propyl methacrylate, butyl methacrylate, or iso-butyl methacrylate.

The hydrophilic monomer of Formula I, Formula II and Formula III has a structure of Formula IV as shown below:

where $R_1$ is, e.g., and $R_2$ is —OCH$_2$CH$_2$OH, —O CH$_2$CH$_2$CH$_2$OH, —O CH$_2$CH(OH)CH$_3$, —O CH$_2$CH$_2$CH$_2$CH$_2$OH, —OCH$_2$CH$_2$SO$_3$H, —OCH$_2$CH$_2$CH$_2$SO$_3$H, -(—CH$_2$CH$_2$O—)$_n$CH$_3$, —OCHO(CH$_2$)$_3$ (tetrahydropyranyl methacrylate), —OCH$_2$CH$_2$SO$_4^-$NH$_4^+$, —NHCH$_2$CH$_2$NHSO$_3^-$NH$_4^+$, —O(CH$_2$CH$_2$O)$_n$-Heparin, —O(CH$_2$CH$_2$O)$_n$-Hyaluronic acid, or —OH.

The polymers described herein can be synthesized by methods known in the art (see, for example, D. Braun, et al., Polymer Synthesis: Theory and Practice. Fundamentals, Methods, Experiments. 3$^{rd}$ Ed., Springer, 2001; Hans R. Kricheldorf, Handbook of Polymer Synthesis, Marcel Dekker Inc., 1992; G. Odian, Principles of Polymerization, 3$^{rd}$ ed. John Wiley & Sons, 1991). For example, free radical methods can be used to make the polymer (see, for example, D. Braun, et al., Polymer Synthesis: Theory and Practice. Fundamentals, Methods, Experiments. 3$^{rd}$ Ed., Springer, 2001; Hans R. Kricheldorf, Handbook of Polymer Synthesis, Marcel Dekker Inc., 1992). Polymerization by suspension or emulsion techniques utilizing free radical initiation is commonly employed. Block copolymers and terpolymers can be produced by atom transfer polymerization. Grafting of hydrophilic monomers onto pre-made poly(vinylidene fluoride-co-hexafluoropropylene) can be accomplished by ozonation of the fluoropolymer followed by thermally induced graft polymerization of the hydrophilic monomer. Polymerization in a solvent can also be used to synthesize the polymers described herein.

Polymer Blends

In another embodiment, the polymer described herein can be blended with one or more additional biocompatible polymers to generate a polymer blend coating material that has the desired flexibility and drug permeability. Generally, useful polymers that can be blended with the polymer defined above include the polymer of Formula I, II and III. The one or more additional biocompatible polymer is described below.

The additional biocompatible polymer can be biodegradable (both bioerodable or bioabsorbable) or nondegradable, and can be hydrophilic or hydrophobic. Hydrophilic is defined to have a δ value greater than about 8.5, e.g., a δ value of about 8.5, about 9.5, about 10.5 or about 11.5. δ value is a hydrophobicity scale commonly used in the art of polymer or protein materials.

Representative biocompatible polymers include, but are not limited to, poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly polyesters, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(etheresters) (e.g. PEO/PLA); polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as HEMA, hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), and combinations thereof. In some embodiments, the polymer can exclude any one of the aforementioned polymers.

As used herein, the terms poly(D,L-lactide), poly(L-lactide), poly(D,L-lactide-co-glycolide), and poly(L-lactide-co-glycolide) can be used interchangeably with the terms poly(D,L-lactic acid), poly(L-lactic acid), poly(D,L-lactic acid-co-glycolic acid), and poly(L-lactic acid-co-glycolic acid), respectively.

Biobeneficial Material

The polymer or polymer blends described above can form a matrix coating or a topcoat, optionally with a biobeneficial material. The biobeneficial material can be optionally coupled to said polymer or polymer blend via covalent, ionic or hydrogen bonding. Covalent bonds can be formed by chemical reaction. The combination can be mixed, blended, or coated in separate layers. The biobeneficial material useful in the coatings described herein can be a polymeric material or non-polymeric material. The biobeneficial material is preferably non-toxic, non-antigenic and non-immunogenic. A biobeneficial material is one which enhances the biocompatibility of a device by being non-fouling, hemocompatible, actively non-thrombogenic, or anti-inflammatory, all without depending on the release of a pharmaceutically active agent.

Representative biobeneficial materials include, but are not limited to, polyethers such as poly(ethylene glycol), copoly (ether-esters) (e.g. PEO/PLA); polyalkylene oxides such as poly(ethylene oxide), polypropylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly (ethylene glycol) acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as CD-34 antibody, fibrin, fibrinogen, cellulose, starch, collagen, dextran, dextrin, hyaluronic acid, fragments and derivatives of hyaluronic acid, heparin, fragments and derivatives of heparin such as heparin sulfate, heparin sulfonate, or PEGylated heparin, glycosamino glycan (GAG), GAG derivatives, polysaccharide, elastin, chitosan, or alginate, silicones, PolyActive™, and combinations thereof. In some embodiments, the coating can exclude any one of the aforementioned polymers.

The term PolyActive™ refers to a block copolymer having flexible poly(ethylene glycol) and poly(butylene terephthalate) blocks (PEGT/PBT). PolyActive™ is intended to include AB, ABA, BAB copolymers having such segments of PEG and PBT (e.g., poly(ethylene glycol)-block-poly(butyleneterephthalate)-block poly(ethylene glycol) (PEG-PBT-PEG).

In a preferred embodiment, the biobeneficial material can be a polyether such as poly (ethylene glycol) (PEG) or polyalkylene oxide.

Release Rate Control Membrane

The biocompatible polymers described in Formula I, II and II and its blends with other biocompatible polymer can be used as a topcoat to control the release rate In addition to membrane function, the polymer can also provide an anchor point for further surface modification to attach bio-beneficial molecules, defined above, on the surface.

Bioactive Agents

The polymeric coatings or the polymeric substrate described herein may optionally include one or more bioactive agents. These bioactive agents can be any agent which is a therapeutic, prophylactic, or diagnostic agent. These agents can have anti-proliferative or anti-inflammatory properties or can have other properties such as antineoplastic, antiplatelet, anti-coagulant, anti-fibrin, antithrombonic, antimitotic, antibiotic, antiallergic, antioxidant as well as cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include methyl rapamycin (ABT-578), 40-O-(3-hydroxy)propyl-rapamycin, 40-O-[2-(2-hydroxy)ethoxy] ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as ANGIOMAX™ (bivalirudin, Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, NJ), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6, 6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, combinations thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, NJ). An example of an antiallergic agent is permirolast potassium. Other therapeutic substances or agents which may be appropriate include alpha-interferon, bioactive RGD, and genetically engineered epithelial cells. The foregoing substances can also be used in the form of prodrugs or co-drugs thereof. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient; the nature of the trauma; the nature of the desired therapy; the time over which the administered ingredient resides at the vascular site; and if other active agents are employed, the nature and type of these agents or combination of agents. Therapeutically effective dosages can be determined empirically, for example by infusing vessels from suitable animal model systems or using immunohistochemical, fluorescent or electron microscopy methods to detect the agent and its effects, or by conducting suitable in vitro studies. Standard pharmacological test procedures to determine dosages are understood by one of ordinary skill in the art.

Examples of Implantable Device

As used herein, an implantable device may be any suitable medical substrate that can be implanted in a human or veterinary patient. Examples of such implantable devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP2ON" consists of 50% cobalt, 20% nickel, 20% chromium, and 10% molybdenum. Devices made from bioabsorbable or biostable polymers could also be used with the embodiments of the present invention. The device itself, such as a stent, can also be made from the described inventive polymers or polymer blends.

Method of Use

In accordance with embodiments of the invention, a coating of the various described embodiments can be formed on an implantable device or prosthesis, e.g., a stent. For coatings including one or more active agents, the agent will be retained on the medical device such as a stent during delivery and expansion of the device, and released at a desired rate and for a predetermined duration of time at the site of implantation. Preferably, the medical device is a stent. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating or preventing occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

EXAMPLES

The embodiments of the present invention will be illustrated by the following examples. All parameters and data are not to be construed to unduly limit the scope of the embodiments of the invention.

Example 1

3×18mm Vision stents were coated with 80 µg poly(butyl methacrylate) (PBMA, Mw=300K, $T_g$=30° C., from ESSCHEM) primer. The primer coating solution was 2% PBMA in 70/30 acetone/cyclohexanone mixture. After the solution was spray-coated on the stents, the stent was baked at 80° C. to cure the primer.

Example 2

Figure 1:
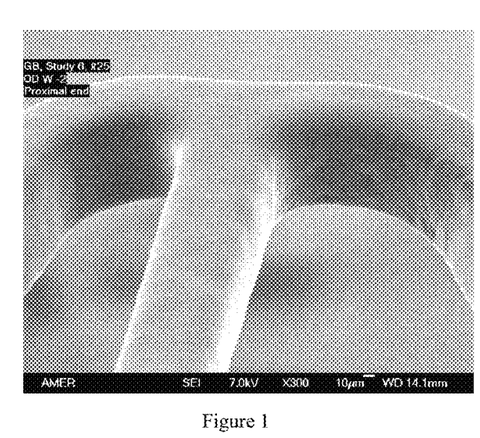
FIG. 1 is a SEM (scanning electron microscopy) picture of a coating formed of poly(methyl methacrylate-co-methacrylic acid) (PMMA-co-MA) after wet expansion.

The drug coating solution was composed of 2% polymer blend and 1.45% everolimus in 30/70 dimethylacetamide (DMAC) and tetrahydrofuran (THF). The polymer blend was made of 75:25 w/w PBMA and poly(methyl methacrylate-co-methacrylic acid) (PMMA-co-MA, molar ratio 1:0.016, $T_g$=105° C. from Aldrich). The solution was spray-coated onto the primer-coated stents. The target drug coat weight was 450 µg. The drug loading was 190 µg. After the coating, the stents were crimped and secured onto the balloon. The stents were over expanded to 3.5 mm in water. The coating integrity was examined with SEM. An SEM picture of the coating after wet expansion is shown in FIG. 1.

The test of the drug release rate of a coated stent was performed in 4% porcine serum albumin in a PBS (phosphate buffered saline) buffer at 37° C. The everolimus release rate at 24 hours was 11% +/−1%.

Example 3

The drug coating solution was composed of 2% polymer blend and 1.45% everolimus in 30/70 dimethylacetamide (DMAC) and tetrahydrofuran (THF). The polymer blend was made of 75:25 w/w PBMA and poly(methyl methacrylate-co-methacrylic acid) (PMMA-co-MA, molar ratio 95:5 from PolySciences). The solution was spray-coated onto the primer-coated stents. The target drug coat weight was 450 µg. The drug loading was 190 µg. After coating, the stents were crimped and secured onto the balloon. The drug release rate was tested in 4% porcine serum albumin in PBS buffer at 37° C. The release rate at 24 hours was 34% +/−2%.

Example 4

The drug coating solution was composed of 2% PMMA-co-MA (Aldrich) and 1.34% everolimus in 30/70 dimethylacetamide (DMAC) and tetrahydrofuran (THF). The solution was spray-coated onto the primer coated stents. The target drug coat weight was 470 μg. The drug loading was 190 μg. After coating, the stents were crimped and secured onto the balloon. The drug release rate was tested in 4% porcine serum albumin in PBS buffer at 37° C. The release rate at 24 hours was 1%.

Example 5

Figure 2:
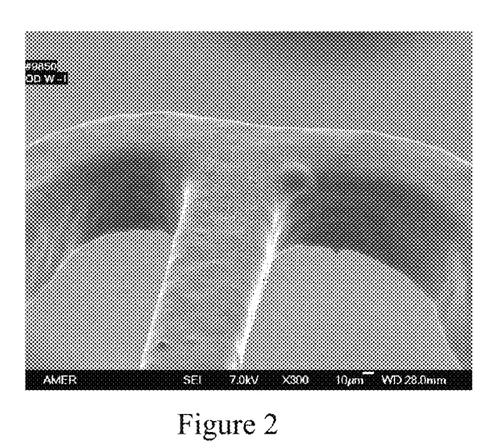
FIG. 2 is a SEM picture of a coating formed of poly(vinylidene fluoride-co-hexafluoropropylene) (PVDF-HFP) and everolimus matrix and a poly(ethyl acrylate-co-acrylic acid).

3×18 mm Vision stents were coated with everolimus in poly(vinylidene fluoride-co-hexafluoropropylene) (PVDF-HFP) matrix and labeled. Drug loading was 200 μg. The topcoat solution was made of 2% poly(ethyl acrylate-co-acrylic acid) (PEA-co-AA, molar ratio 50:50, from PolySciences) in 30/70 cyclohexanone and acetone mixture. The topcoat solution was spray-coated onto the labelled stents. After drying the coating, the stents were reweighed and the topcoat weight was 100 μg. Three stents were then wet expanded and the coating integrity was checked using SEM. FIG. 2 is a representative picture. The drug was extracted in acetonitrile and analyzed with HPLC. Drug content was unchanged with and without topcoat. The drug release rate was tested in a 4% PSA/PBS solution. The release rate at 24 hours was not changed with and without topcoat, indicating that the topcoat was permeable to the drug.

Top-coated stents were then immersed into 4% PEG/water and shaken at room temperature for 4 hours to mimic a heparin coupling reaction process. Afterwards, the stents were rinsed with water and dried in vacuum at 50° C. for 8 hours. The drug was extracted in acetonitrile and analyzed with HPLC, and drug release was measured in PSA/PBS solution at 24 hour time point. Drug content was not changed with the aqueous wash. However, the drug release rate decreased from 25% to 20%. Drug purity was also analyzed with HPLC and the impurity content was not significantly increased.

The experimental results showed that the carboxylated group on the topcoat can be coupled to the amido-reaction groups on many biological molecules, such as CD-34 antibody, heparin, PEG-NH$_2$, through a water phase coupling reaction.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A biocompatible polymer comprising a hydrophobic monomer and hydrophilic monomer[s], the biocompatible polymer having a backbone structure comprising at least a tertiary carbon grouping; and the biocompatible polymer being of the structure of formula I:

-[-Hydrophobic monomer-]$_m$-[-Hydrophilic monomer-]$_n$-　　　　Formula I wherein m and n can be positive integers from 1 to 100,000;

wherein the hydrophobic monomer can be a methacrylate or fluorinated methacrylate;

wherein the hydrophilic monomer is a residue of the structure of formula IV:

Formula IV wherein R$_1$ is and

R$_2$ is —OCH$_2$CH$_2$SO$_4^-$NH$_4^+$, —NHCH$_2$CH$_2$NHSO$_3^-$NH$_4^+$, —O(CH$_2$CH$_2$O)$_n$-Heparin, or —O(CH$_2$CH$_2$O)$_n$-Hyaluronic acid;

or the biocompatible polymer being of the structure of formula III:

-[-Hydrophobic monomer-]$_m$-[-Hydrophilic monomer 1-]$_n$-[-Hydrophilic monomer 2-]$_p$-　　　　Formula III wherein the hydrophilic monomer 1 and the hydrophilic monomer 2 of Formula III are residues of the structure of formula IV:

Formula IV wherein m, n, and p are independently positive integers ranging from 1 to 100,000;

wherein the hydrophobic monomer is a methacrylate or fluorinated methacrylate, and hydrophilic monomer 1 and hydrophilic monomer 2 are different;

and wherein for both the hydrophilic monomer 1 and the hydrophilic monomer 2, R$_1$ is wherein, for the hydrophilic monomer 1, R$_2$ is —OCH$_2$CH$_2$SO$_4^-$NH$_4^+$, —NHCH$_2$CH$_2$NHSO$_3^-$NH$_4^+$, —O(CH$_2$CH$_2$O)$_n$-Heparin, or —O(CH$_2$CH$_2$O)$_n$-Hyaluronic acid;

and wherein, for the hydrophilic monomer 2, R$_2$ is —OCH$_2$CH$_2$OH, —O CH$_2$CH$_2$CH$_2$OH, —O CH$_2$CH(OH)CH$_3$, —O CH$_2$CH$_2$CH$_2$CH$_2$OH, —OCH$_2$CH$_2$SO$_3$H, —OCH$_2$CH$_2$CH$_2$SO$_3$H, —(—CH$_2$CH$_2$O—)$_n$CH$_3$, —OCHO(CH$_2$)$_3$(tetrahydropyranyl methacrylate), or —OH.

2. The biocompatible polymer of claim 1, wherein the biocompatible polymer is of the structure of formula I.

3. The biocompatible polymer of claim 1, wherein the biocompatible polymer is of the structure of formula III.

4. The biocompatible polymer of claim 1, wherein the biocompatible polymer is of the structure of formula I and $R_2$ of the hydrophilic monomer of the biocompatible polymer of the structure of formula I is —$OCH_2CH_2SO_4^-NH_4^+$.

5. The biocompatible polymer of claim 1, wherein the biocompatible polymer is of the structure of formula I and $R_2$ of the hydrophilic monomer of the biocompatible polymer of the structure of formula I is —$NHCH_2CH_2NHSO_3^-NH_4^+$.

6. The biocompatible polymer of claim 1, wherein the biocompatible polymer is of the structure of formula I and $R_2$ of the hydrophilic monomer of the biocompatible polymer of the structure of formula I is —$O(CH_2CH_2O)_n$-Heparin.

7. The biocompatible polymer of claim 1, wherein the biocompatible polymer is of the structure of formula I and $R_2$ of the hydrophilic monomer of the biocompatible polymer of the structure of formula I is —$O(CH_2CH_2O)_n$-Hyaluronic acid.

8. The biocompatible polymer of claim 1, wherein the biocompatible polymer is of the structure of formula III and $R_2$ of the hydrophilic monomer 1 of the biocompatible polymer of the structure of formula III is —$OCH_2CH_2SO_4^-NH_4^+$.

9. The biocompatible polymer of claim 1, wherein the biocompatible polymer is of the structure of formula III and $R_2$ of the hydrophilic monomer 1 of the biocompatible polymer of the structure of formula III is —$O(CH_2CH_2O)_n$-Heparin.

10. The biocompatible polymer of claim 1, wherein the biocompatible polymer is of the structure of formula III and $R_2$ of the hydrophilic monomer 1 of the biocompatible polymer of the structure of formula III is —$O(CH_2CH_2O)_n$-Hyaluronic acid.

11. The biocompatible polymer of claim 1, wherein the biocompatible polymer is of the structure of formula III and $R_2$ of the hydrophilic monomer 1 of the biocompatible polymer of the structure of formula III is —$NHCH_2CH_2NHSO_3^-NH_4^+$.

12. An implantable device having a biocompatible coating thereon, wherein the biocompatible coating comprises the biocompatible polymer of claim 1.

13. The implantable device according to claim 12, wherein the coating further comprises a bio-beneficial material.

14. The implantable device according to claim 12, wherein the biocompatible coating further comprises at least one additional polymer.

15. The implantable device according to claim 14, wherein the one additional polymer is selected from the group consisting of poly(ester amides), polyhydroxyalkanoates (PHA), poly(3-hydroxyalkanoates), poly(4-hydroxyalknaotes), polymers and copolymers comprising a monomer selected from the group consisting of 3-hydroxypropanoate, 3-hydroxybutyrate, 3-hydroxyvalerate, 3-hydroxyhexanoate, 3-hydroxyheptanoate, 3-hydroxyoctanoate, 4-hydroxybutyrate, 4-hydroxyvalerate, 4-hydroxyhexanote, 4-hydroxyheptanoate, and 4-hydroxyoctanoate, poly(D,L-lactide), poly (L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(anhydrides), poly (tyrosine carbonates), poly(tyrosine ester), poly(imino carbonates), poly(glycolic acid-co-trimethylene carbonate), polyphosphoesters, polyphosphoester urethanes, poly(amino acids), polycyanoacrylates, poly(trimethylene carbonate), poly(iminocarbonates), polyphosphazenes, silicones, polyesters, polyolefins, polyisobutylene and ethylene-alphaolefin copolymers, acrylic polymers and copolymers, vinyl halide polymers and copolymers, polyvinyl chloride, polyvinyl ethers, polyvinyl methyl ether, polyvinylidene halides, polyvinylidene chloride, polyacrylonitrile, polyvinyl ketones, polyvinyl aromatics, polystyrene, polyvinyl esters, polyvinyl acetate, copolymers of vinyl monomers with each other and olefins, ethylene-methyl methacrylate copolymers, acrylonitrile-styrene copolymers, ABS resins, ethylene-vinyl acetate copolymers, poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), polyamides, Nylon 66, polycaprolactam, alkyd resins, polycarbonates, polyoxymethylenes, polyimides, polyethers, poly(glyceryl sebacate), poly(propylene fumarate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers, poly(ether-esters), poly(ethylene oxide-co-lactic acid) (PEO/PLA), polyalkylene oxides, poly(propylene oxide), polyalkylene oxalates, polyphosphazenes, phosphoryl choline, poly(aspirin), polymers and co-polymers of hydroxyl bearing monomers, HEMA, hydroxypropyl methacrylate (HPMA), hydroxypropyl-methacrylamide, PEG acrylate (PEGA), PEG methacrylate, 2-methacryloyl-oxyethyl-phosphorylcholine (MPC) and n-vinyl pyrrolidone (VP), carboxylic acid bearing monomers, methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), PLURONIC™ surfactants (polypropylene oxide-co-polyethylene glycol), poly(tetramethylene glycol), hydroxy functional poly(vinyl pyrrolidone), glycosamino glycan (GAG), and combinations thereof.

16. The implantable device according to claim 15, wherein the biocompatible polymer of the biocompatible coating comprises the biocompatible polymer of formula I.

17. The implantable device according to claim 16, wherein the coating further comprises a bio-beneficial material.

18. The implantable device according to claim 15, wherein the biocompatible polymer of the biocompatible coating comprises the biocompatible polymer of formula III.

19. The implantable device according to claim 18, wherein the coating further comprises a bio-beneficial material.

20. The implantable device according to claim 12, which is a drug delivery stent, and wherein the coating further comprises a bioactive agent.

21. The drug delivery stent of claim 20, wherein the bioactive agent is selected from the group consisting of paclitaxel, docetaxel, estradiol, nitric oxide donors, super oxide dismutases, 4-amino-2,2,6,6-tetramethylpiperidine-1-oxyl (4-amino-TEMPO), tacrolimus, dexamethasone, rapamycin, 40—O—(2-hydroxy)ethyl-rapamycin (everolimus), 40—O—(3-hydroxy)propyl-rapamycin, 40—O—[2-(2-hydroxy)ethoxy]ethyl-rapamycin, 40-O-tetrazole-rapamycin, ABT-578, clobetasol, and combinations thereof.

22. The drug delivery stent of claim 21, wherein the biocompatible polymer of the biocompatible coating comprises the biocompatible polymer of formula I.

23. A method of treating a disorder in a patient comprising implanting in the patient the drug delivery stent of claim 22, wherein the disorder is selected from the group consisting of atherosclerosis, thrombosis, restenosis, hemorrhage, vascular dissection or perforation, vascular aneurysm, vulnerable plaque, chronic total occlusion, patent foramen ovale, claudication, anastomotic proliferation for vein and artificial grafts, bile duct obstruction, ureter obstruction, tumor obstruction, and combinations thereof.

24. The drug delivery stent of claim 21, wherein the biocompatible polymer of the biocompatible coating comprises the biocompatible polymer of formula III.

25. A method of treating a disorder in a patient comprising implanting in the patient the drug delivery stent of claim 24, wherein the disorder is selected from the group consisting of atherosclerosis, thrombosis, restenosis, hemorrhage, vascular dissection or perforation, vascular aneurysm, vulnerable plaque, chronic total occlusion, patent foramen ovale, claudication, anastomotic proliferation for vein and artificial grafts, bile duct obstruction, ureter obstruction, tumor obstruction, and combinations thereof.

26. The implantable device according to claim 12, wherein the biocompatible polymer of the biocompatible coating is of the structure of formula I.

27. The implantable device according to claim 26, wherein $R_2$ of the hydrophilic monomer of the biocompatible polymer of the structure of formula I is —$OCH_2CH_2SO_4^-NH_4^+$.

28. The implantable device according to claim 26, wherein $R_2$ of the hydrophilic monomer of the biocompatible polymer of the structure of formula I is —$NHCH_2CH_2NHSO_3^{-NH}{}_4^+$.

29. The implantable device according to claim 26, wherein $R_2$ of the hydrophilic monomer of the biocompatible polymer of the structure of formula I is —$O(CH_2CH_2O)_n$-Heparin.

30. The implantable device according to claim 26, wherein $R_2$ of the hydrophilic monomer of the biocompatible polymer of the structure of formula I is —$O(CH_2CH_2O)_n$-Hyaluronic acid.

31. The implantable device according to claim 12, wherein the biocompatible polymer of the biocompatible coating is of the structure of formula III.

32. The implantable device according to claim 31, wherein $R_2$ of the hydrophilic monomer 1 of the biocompatible polymer of the structure of formula III is —$OCH_2CH_2SO_4^-NH_4^+$.

33. The implantable device according to claim 31, wherein $R_2$ of the hydrophilic monomer 1 of the biocompatible polymer of the structure of formula III is —$NHCH_2CH_2NHSO_3^-NH_4^+$.

34. The implantable device according to claim 31, wherein $R_2$ of the hydrophilic monomer 1 of the biocompatible polymer of the structure of formula III is —$O(CH_2CH_2O)_n$-Heparin.

35. The implantable device according to claim 31, wherein $R_2$ of the hydrophilic monomer 1 of the biocompatible polymer of the structure of formula III is —$O(CH_2CH_2O)_n$-Hyaluronic acid.

* * * * *